(12) United States Patent
Cochran (10) Patent No.: US 7,008,104 B2
(45) Date of Patent: Mar. 7, 2006

(54) DENTAL X-RAY FILM POSITIONING INSTRUMENT

(76) Inventor: Phillip E. Cochran, 5632 NW. 204th Pl., Portland, OR (US) 97229

( * ) Notice: Subject to any disclaimer, the term of this patent is extended or adjusted under 35 U.S.C. 154(b) by 0 days.

(21) Appl. No.: 10/623,374

(22) Filed: Jul. 18, 2003

(65) Prior Publication Data
US 2005/0013413 A1    Jan. 20, 2005

(51) Int. Cl.
*A61B 6/14*    (2006.01)
(52) U.S. Cl. ...................................... 378/170; 378/205
(58) Field of Classification Search ........ 378/168–170, 378/191, 38, 205
See application file for complete search history.

(56) References Cited

U.S. PATENT DOCUMENTS

| | | | | |
|---|---|---|---|---|
| 1,465,516 A | * | 8/1923 | Hallenberg | 378/168 |
| 1,576,477 A | * | 3/1926 | Wiens | 378/168 |
| 1,923,669 A | | 8/1933 | Harrison | 378/170 |
| 2,245,395 A | | 6/1941 | Goldberg | 378/170 |
| 2,285,943 A | * | 6/1942 | Riesenfeld | 378/205 |
| 2,688,096 A | | 8/1954 | Galliano et al. | 378/168 |
| 3,473,026 A | * | 10/1969 | Updegrave | 378/170 |
| 4,048,506 A | | 9/1977 | Updegrave | 250/479 |
| 4,057,732 A | | 11/1977 | Klauser | 250/479 |
| 4,295,050 A | | 10/1981 | Linden | 250/479 |
| 4,365,162 A | | 12/1982 | Jarby | 378/170 |
| 4,598,416 A | | 7/1986 | Donato | 378/168 |
| 4,949,370 A | | 8/1990 | Tanaka | 378/170 |
| 5,422,927 A | | 6/1995 | Schmitz | 378/170 |
| 5,737,388 A | | 4/1998 | Kossila | 378/168 |
| 6,041,102 A | | 3/2000 | Francsis | 378/165 |

FOREIGN PATENT DOCUMENTS

| | | |
|---|---|---|
| DE | 642 156 | 2/1937 |
| DE | 836 835 | 7/1949 |
| GB | 530440 | 12/1940 |

* cited by examiner

*Primary Examiner*—Craig E. Church
*Assistant Examiner*—Jurie Yun
(74) *Attorney, Agent, or Firm*—Kolisch Hartwell, P.C.

(57) ABSTRACT

An instrument for aligning an x-ray beam relative to an x-ray film and a target tooth of an animal patient. The instrument orients the beam relative to the film, to produce dental radiographs of the target tooth in accordance with the bisecting-angle technique. More specifically, the instrument includes an alignment tool configured to align a longitudinal axis of the x-ray beam orthogonal to a bisecting plane lying approximately midway between a target plane defined by the target tooth, and an x-ray film plane defined by the x-ray film. In some embodiments, the instrument may also include an x-ray film holder and an x-ray film holder support, allowing the film to be conveniently positioned and held in proper alignment during an x-ray procedure.

15 Claims, 5 Drawing Sheets

DENTAL X-RAY FILM POSITIONING INSTRUMENT

FIELD OF THE INVENTION

The invention relates to dental instruments for animal patients. More particularly, the invention relates to an instrument for aligning an x-ray beam with a desired orientation relative to a target tooth of an animal patient, in accordance with the bisecting-angle technique.

BACKGROUND OF THE INVENTION

Various conditions can adversely affect the dental health of animal patients such as dogs and cats. If untreated, these conditions can develop into more serious illnesses, possibly leading to debilitating diseases and even death. For example, although the presence of quantities of bacteria in the mouth of a patient is normal, if the numbers of bacteria become too large they can lead to periodontitis, or periodontal disease. Periodontal disease frequently results in loss of teeth, and may also lead to serious bacterial infections and related illnesses if left untreated, as described below.

Periodontal disease in animals typically leads to recession of the gingiva (gums) in areas surrounding the diseased teeth. This recession of the gums may advance far enough so that a tooth becomes loose, at which point large quantities of bacteria may be released into the blood stream. Bacteria released by periodontitis in this manner may travel to any part of the body, including the heart, lungs, and kidneys, possibly leading to serious infections of those organs. Animals must therefore receive periodic dental care in order to prevent and/or treat periodontal disease, and to remain healthy.

In addition to periodontal disease, other dental conditions in animals may require examination and/or treatment by a veterinarian. These include, for example, chipped or broken teeth, abscesses, caries (cavities), and oral lesions of various types, among others. Accurate dental x-rays are crucial for the pre-treatment diagnosis of these conditions, and also often are used to confirm that treatment has been successful. For instance, dental x-rays may aid in the pre-treatment diagnosis of an abscessed tooth, and also may be used after a root canal procedure, to verify that the pulp cavity and root canal have been completely filled.

Dental x-rays are typically obtained by directing a collimated x-ray beam from an x-ray head towards an intraoral x-ray film, with one or more target teeth of the patient disposed between the x-ray head and the film. The least distortion of the resulting radiographic image occurs when the x-ray film and the target teeth are parallel to each other and orthogonal to the beam, with the film just behind the target teeth. However, for most animal patients, this parallel technique is only possible when obtaining x-rays of the lower rear teeth (caudal mandibular view). For all other views, the shape of the animal's palate and/or other factors prevent using the parallel technique, and the least distortion is obtained using the bisecting-angle technique.

In the bisecting-angle technique, an x-ray film plane is defined by the plane of the x-ray film, and a target plane is defined by an axis through a target tooth. A bisecting plane is defined by the angle that bisects the x-ray film plane and the target plane, and the x-ray beam is directed orthogonal to the bisecting plane. This technique leads to a radiographic image in which the image of the target tooth has approximately the same height as the tooth itself. More specifically, portions of the image corresponding to cross sections of the target tooth taken parallel to the target plane have the same sizes in the x-ray as the corresponding actual cross sections of the tooth.

Typically, a veterinarian or a veterinary technician estimates the target plane, the bisecting angle, and the corresponding bisecting plane by inspection during an x-ray procedure. Furthermore, aligning the x-ray beam orthogonal to the estimated bisecting plane also typically is done by inspection. In some cases, this procedure may lead to errors in determining the bisecting plane and/or aligning the x-ray beam orthogonal to the bisecting plane. This may result in foreshortened, elongated, and/or otherwise distorted radiographic images on the film.

SUMMARY OF THE INVENTION

An instrument for aligning a collimated x-ray beam relative to an x-ray film and a target tooth of an animal patient is provided. The instrument orients the beam relative to the film, to produce dental radiographs of the target tooth in accordance with the bisecting-angle technique. More specifically, the instrument is configured to align a longitudinal axis of the x-ray beam orthogonal to a bisecting plane that lies approximately midway between a target plane defined by the target tooth, and an x-ray film plane defined by the x-ray film. In general, alignment of the x-ray beam is accomplished by orienting a portion of the instrument at a known angle relative to the bisecting plane, and attaching an x-ray alignment assembly to that portion.

In one embodiment, alignment of the x-ray beam is accomplished by orienting a first handle of the instrument parallel to the x-ray film plane, and orienting a second handle of the instrument parallel to the target plane. A bisecting member is provided and is adapted to lie parallel to the bisecting plane when the first and second handles of the instrument are aligned parallel to the x-ray film plane and the target plane, respectively. Once the orientation of the bisecting plane is established, a targeting ring attached to the bisecting member may be used to align the x-ray beam orthogonal to the bisecting plane.

In some embodiments, the instrument may also include an x-ray film holder and an x-ray film holder support, allowing the film to be conveniently positioned and held in proper alignment during an x-ray procedure. A guiding member may also be included, for accurately estimating the target plane.

DETAILED DESCRIPTION OF THE INVENTION

Figure 1:
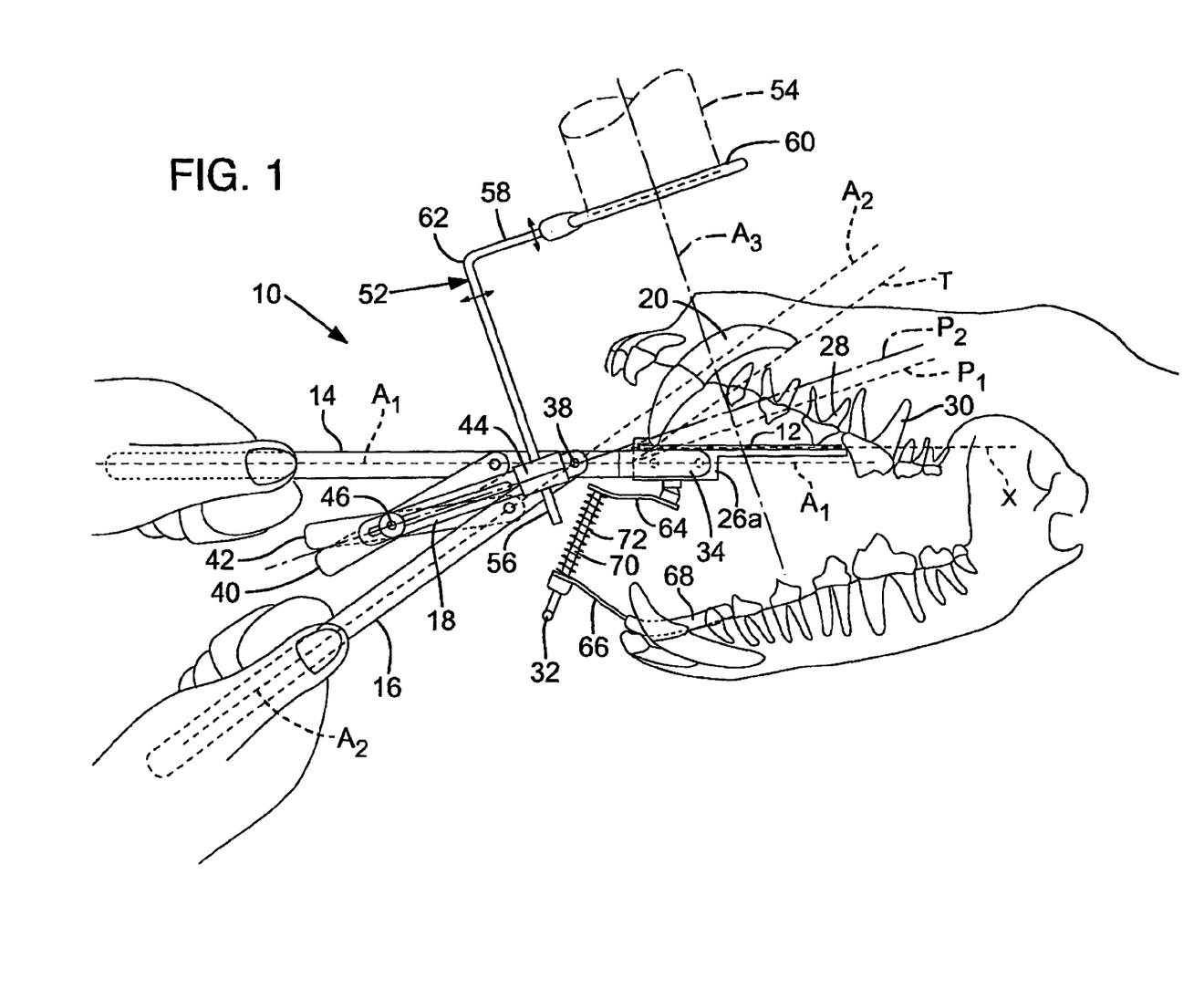
FIG. 1 is a side elevational view of an embodiment of a positioning instrument being used to obtain a relatively undistorted radiograph of an upper canine tooth of an animal patient, in accordance with the bisecting-angle technique.
Figure 2:
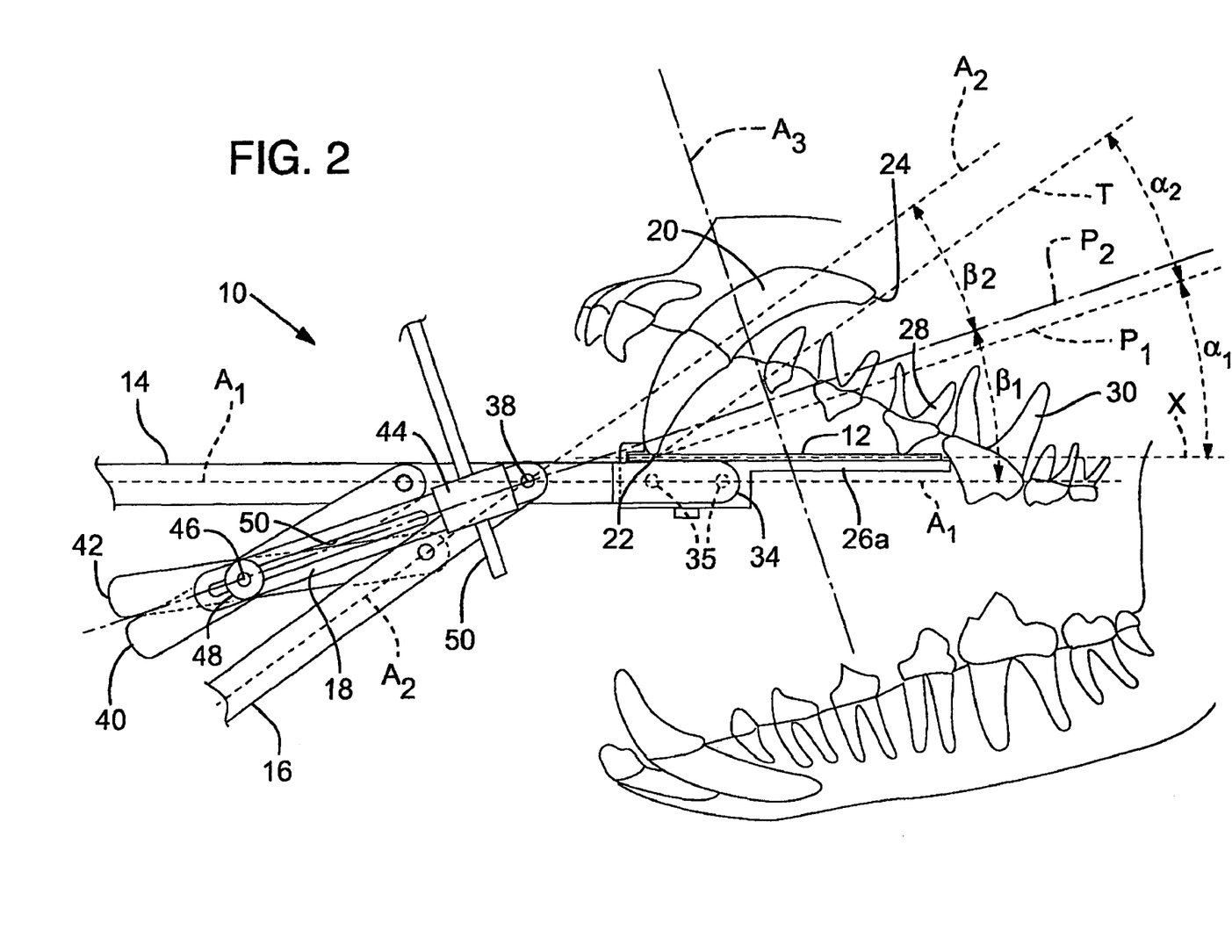
FIG. 2 is a magnified view of a central portion of FIG. 1, showing proper alignment of the positioning instrument.

FIGS. 1–2 depict an exemplary embodiment of a dental alignment instrument, generally indicated at 10, being used to position an x-ray film 12 in the mouth of an animal patient to obtain a maxillary view of a canine target tooth. For clarity, only the teeth and jaws of the animal patient are shown. The depicted embodiment of instrument 10 generally includes a first handle 14 having a longitudinal axis $A_1$, a second handle 16 pivotally attached to the first handle and having a longitudinal axis $A_2$, and a bisecting member 18 configured to bisect the angle between the first and second handles.

X-ray film 12 is substantially planar, and extends perpendicular to the plane of FIG. 1, defining an x-ray film plane X whose intersection with the plane of FIG. 1 is represented by a dashed line. (Similarly, various other planes of interest are represented in the drawings as dashed lines, each dashed line representing the intersection of a plane of interest with the plane of the drawing in which it is depicted.) Instrument 10 may be used to align a collimated x-ray beam relative to x-ray film plane X, such that the bisecting-angle technique may be used to obtain a dental radiograph, as described below.

Still referring to FIGS. 1–2, a target tooth 20, taken to be an upper canine tooth, defines a target plane T. According to one conventional method, target plane T is defined by a line connecting tip 22 of the target tooth to apex 24 of its root, as indicated in FIG. 2. However, other conventions for choosing a target plane are possible. For example, the target plane may be defined to include the planar cross section of the target tooth that has the greatest two-dimensional area.

Regardless of the convention by which it is chosen, the significance of the target plane is that in x-rays taken using the bisecting-angle technique, the target plane defines the orientation of cross sections within the target in which objects will be represented in an x-ray with the least distortion. Specifically, cross sections of the target that are oriented parallel to the target plane will be represented in an x-ray without distortion, whereas cross sections of the target with other orientations will be represented in an x-ray with at least some distortion. The distortion typically takes the form of elongation or foreshortening.

The target plane may in some circumstances be selected in a manner depending upon the condition of the particular target tooth of interest in a given x-ray procedure. For instance, if there is damage or suspected damage to the target tooth that extends substantially within a particular plane, it may be desirable to choose the target plane to coincide with the plane of the tooth damage. This may be the case even if the plane of tooth damage or suspected tooth damage is substantially different than a conventionally defined target plane.

In a typical veterinary x-ray procedure, the patient is sedated, x-ray film 12 is placed in a film holder, and the film holder is positioned intraorally, adjacent to the target tooth and possibly abutting one or more nontarget teeth for stability. In FIGS. 1–2, for example, a film holder 26a is shown abutting a third premolar tooth 28 and a fourth premolar tooth 30. As described previously, film 12 is planar and defines an x-ray film plane X. A film holder support 32, to be described in more detail below, may be used to conveniently hold film holder 26a in place and to keep the patient's mouth open during the x-ray procedure.

Figure 3A:
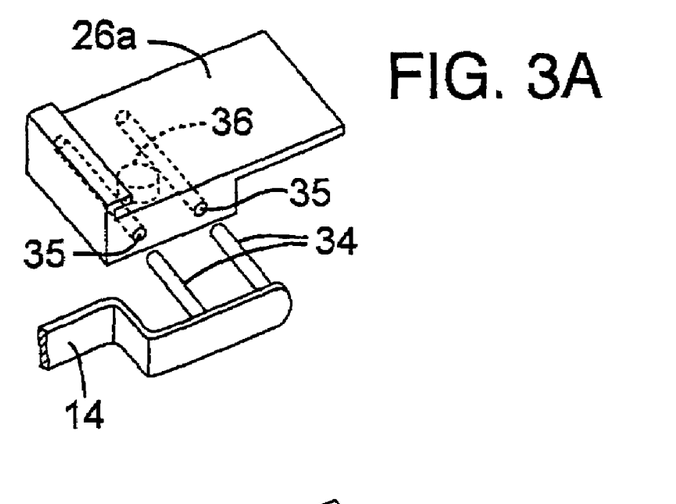
FIG. 3A is an isometric view of an x-ray film holder showing a handle of a dental positioning instrument in position to be attached to the film holder.
Figure 3B:
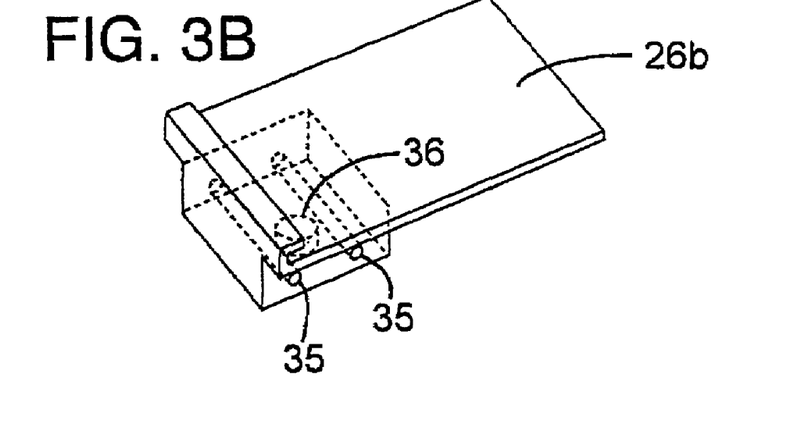
FIG. 3B is an isometric view of another x-ray film holder.
Figure 3C:
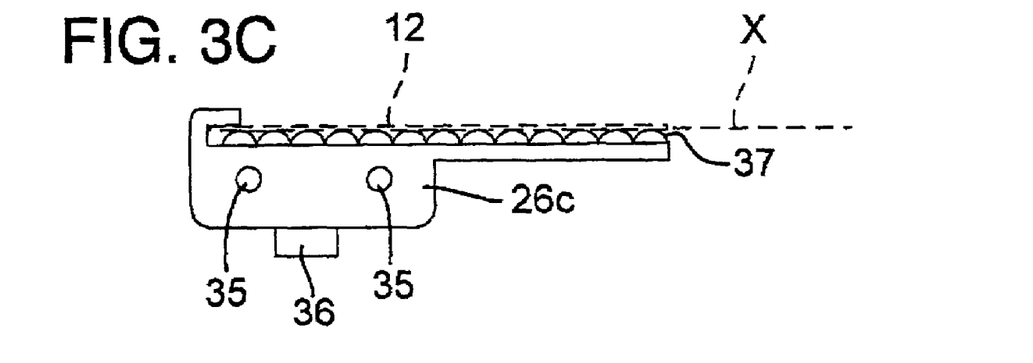
FIG. 3C is a side elevational view of yet another x-ray film holder.

Once a film holder has been properly located within the patient's mouth, first handle 14 of instrument 10 is configured to securely engage the film holder. FIGS. 3A–3C show several film holders 26a–c, which are suitable for use with instrument 10. Handle 14 engages each film holder via a pair of pegs 34 that are inserted into a pair of corresponding apertures 35. Pegs 34 and apertures 35 are depicted as cylindrical, but may take any desired shape. Apertures 35 may extend completely through each film holder, so that handle 14 may be selectively attached to either side of the holder depending upon the specific application. Each of film holders 26a–c also includes a protruding detent, depicted in FIGS. 3A–C as a cylindrical detent 36, for engaging film holder support 32.

Film holders 26a–c are interchangeable, and a particular film holder may be especially suitable for a given application. For example, film holder 26a of FIG. 3A (also shown in FIGS. 1, 2, and 4) is a standard-sized film holder that may be suitable for obtaining dental x-rays from an adult cat or a small dog. Alternatively, film holder 26b of FIG. 3B accommodates a larger x-ray film, and may be more suitable for use with a larger patient. FIG. 3C depicts another film holder 26c, including a plurality of arcuate ridges 37 defining a top surface of the film holder to support x-ray film 12. Ridges 37 may frictionally engage film 12 to a greater extent than a substantially flat surface, so that film holder 26c may hold the film in a particularly secure manner.

When first handle 14 is engaged with any of film holders 26a–c, for example via insertion of pegs 34 into apertures 35, longitudinal axis $A_1$ of the first handle is oriented substantially parallel to x-ray film plane X. In general, however, it is sufficient that the first handle be engaged with its longitudinal axis oriented at a known angle relative to the x-ray film plane, as will be discussed further below.

Second handle 16, which has longitudinal axis $A_2$, is pivotally attached to the first handle, forming a variable angle between the handles. Handles 14 and 16 may be attached, for example, via a rotatable pin 38, or by any other suitable means including a rivet or a hinge mechanism. Once the first handle is engaged with the film holder, the second handle may be pivoted until its longitudinal axis $A_2$ is oriented substantially parallel to target plane T, as depicted in FIGS. 1–2. In some embodiments, to be described in more detail below, the target plane may be estimated using a specialized guiding member. In this case, axis $A_2$ may coincide with the target plane when the second handle is oriented properly (see, e.g., FIG. 4). In general, it is sufficient that the second handle be engaged with its longitudinal axis oriented at a known angle relative to the target plane.

FIG. 2 shows a magnified view of a central portion of FIG. 1, indicating parallel orientation of handles 14 and 16 relative to x-ray film plane X and target plane T, respectively. A bisecting plane $P_1$ is defined such that angle $\alpha_1$ between plane $P_1$ and x-ray film plane X is equal to angle $\alpha_2$ between plane $P_1$ and target plane T. In other words, plane $P_1$ bisects the total angle $(\alpha_1+\alpha_2)$ between the x-ray film plane and the target plane. According to the bisecting-angle technique, it is desirable to direct an x-ray beam orthogonally towards bisecting plane $P_1$, in order to obtain an image of the target tooth that is as undistorted as possible.

Still referring to FIG. 2, bisecting member 18 is configured to bisect the variable angle between handles 14 and 16. The longitudinal axis of the bisecting member defines a plane $P_2$ which, as described below, is orientable parallel to bisecting plane $P_1$. A pair of rigid coupling members 40 and 42 pivotally connect the bisecting member to the handles, and a mount portion 44 is slidably attached to the bisecting member. The mount portion extends in slight lateral relief away from the bisecting member (out of the plane of FIG.

1), and is configured to slide along the bisecting member in a direction parallel to plane $P_2$. Coupling members 40 and 42 are pivotally attached to the bisecting member and to each other at a movable attachment point 46, and each coupling member is pivotally attached to one of handles 14 and 16.

A pivotal and movable connection of the coupling members to the bisecting member may be made in any suitable manner. For example, a thumbscrew assembly 48 or similar mechanism may be provided at attachment point 46, possibly including one or more low friction washers (not shown) between the various members. Loosening the thumbscrew allows assembly 48 to slide within a slot 50 in bisecting member 18, so that attachment point 46 moves along the length of the bisecting member as the angle between handles 14 and 16 is varied.

The connection at point 46 allows members 40 and 42 to be coupled to bisecting member 18 so that the same length of each coupling member separates the bisecting member from handles 14 and 16. Since the locus of points equidistant from the two handles is the plane that bisects the angle between the handles, this ensures that plane $P_2$, defined by the long axis of the bisecting member, also bisects the angle between the handles. More specifically, bisecting member 18 is configured such that an angle $\beta_1$ between plane $P_2$ and longitudinal axis $A_1$ of first handle 14 is equal to an angle $\beta_2$ between plane $P_2$ and longitudinal axis $A_2$ of second handle 16. In other words, plane $P_2$ bisects the total angle $(\beta_1+\beta_2)$ between axes $A_1$ and $A_2$ of the two handles.

FIG. 2 best shows the geometry most relevant to the structure of instrument 10. As FIG. 2 depicts, when instrument 10 is oriented properly, axis $A_1$ of handle 14 is oriented parallel to x-ray film plane X, and axis $A_2$ of handle 16 is oriented parallel to target plane T. Therefore, plane $P_2$, which bisects the angle between axes $A_1$ and $A_2$, is oriented parallel to plane $P_1$, which bisects the angle between x-ray film plane X and target plane T. Thus, the instrument provides a mechanism for reliably determining the orientation of bisecting plane $P_1$, by aligning plane $P_2$ parallel to plane $P_1$. Since plane $P_2$ intersects bisecting member 18 along its longitudinal axis, the bisecting member therefore also will be oriented parallel to the bisecting plane.

Once bisecting member 18 is oriented parallel to bisecting plane $P_1$, the bisecting member may be used to facilitate aligning a collimated x-ray beam in order to obtain a relatively undistorted image of a target object. According to the bisecting-angle technique, an undistorted image is obtained by directing a collimated x-ray beam towards the target tooth in a direction orthogonal to the bisecting plane. As described in more detail below, this may be accomplished by attaching an alignment assembly to the bisecting member to align an x-ray head with its longitudinal axis orthogonal to the bisecting plane.

Although in the depicted embodiments, bisecting member 18 is shown oriented parallel to bisecting plane $P_1$, it should be appreciated that in general, it is sufficient to orient any reference portion of the alignment instrument (such as the bisecting member) at any known reference angle relative to the bisecting plane. Then the longitudinal axis of the x-ray beam can be aligned at an alignment angle relative to the reference portion, such that the longitudinal axis of the x-ray beam is orthogonal to the bisecting plane. The alignment angle is correlated to the reference angle, and is typically just 90 degrees minus the reference angle. For example, if the reference portion is angled at 60 degrees relative to the bisecting plane, the x-ray beam should be aligned at 30 degrees relative to the reference portion in order to be orthogonal to the bisecting plane.

Various embodiments of the alignment instrument, including those depicted in FIGS. 1, 2, 4, and 5, may include two handles bisected by a bisecting member. In this case, alignment can be accomplished if the first handle is oriented at a known first angle relative to x-ray film plane X, and the second handle is oriented at a known second angle relative to target plane T. The orientation of the bisecting member relative to the bisecting plane can then be deduced from these known angles. Once the orientation of the bisecting member relative to the bisecting plane is known, an alignment assembly may be designed to provide proper alignment for the x-ray beam. The specific design of the alignment assembly depends on the known orientation of the bisecting member relative to the bisecting plane.

Returning to the specific embodiments depicted in the drawings, once a plane parallel to the bisecting plane has been established, as by plane $P_2$ in FIGS. 1–2, an x-ray beam may be directed orthogonal to the bisecting plane by any suitable method. In the embodiment of FIG. 1, instrument 10 includes an x-ray alignment assembly 52, slidably attached to mount portion 44 and configured to align an x-ray beam in accordance with the bisecting-angle technique. In FIG. 1, a standard x-ray collimator 54 is shown. Collimator 54 is configured to emit a substantially collinear x-ray beam in a region centered around a longitudinal axis $A_3$, so that different parts of the beam reach the target from approximately the same direction. Coupling the x-ray alignment assembly to the bisecting member allows longitudinal axis $A_3$ of the x-ray beam to be accurately aligned orthogonal to the bisecting plane.

More particularly, x-ray alignment assembly 52 includes a first end portion 56 attached to mount portion 44, and a second end portion 58 configured to support a standard targeting ring 60 for orienting collimator 54. The targeting ring is adapted to securely engage the collimator, and may include an engagement mechanism, such as an inner circumference (not shown) contoured to match an outer surface of the collimator, for this purpose. First end portion 56 of the alignment assembly is attached orthogonally to bisecting member 18, and an intermediate right angle 62 causes second end portion 58 and targeting ring 60 to each be disposed parallel to bisecting member 18. Thus, x-ray collimator 54 is aligned so that longitudinal axis $A_3$ of the x-ray beam is orthogonal to the bisecting member, and therefore also is orthogonal to bisecting plane $P_1$, in accordance with the bisecting-angle technique.

X-ray alignment assembly 52 may also include various adjustment mechanisms for adjusting position of collimator 54 relative to the target. For example, end portion 56 may be frictionally and slidably engaged with mount portion 44, so that targeting ring 60 can be moved towards and away from the target along axis $A_3$. Similarly, mount portion 44 may be frictionally and slidably engaged with bisecting member 18, allowing motion of the x-ray alignment assembly parallel to the bisecting member. This allows targeting ring 60 to be moved parallel to the bisecting plane until the x-ray beam is substantially centered on the target.

As depicted in FIG. 1, film holder support 32 may be used to hold film holder 26a in stable alignment within the patient's mouth. In the embodiment of the film holder support depicted in FIG. 1, a first support member 64 is placed against cylindrical detent 36 of film holder 26a, and a second support member 66 is placed against one or more nontarget teeth of the patient. Member 66 may include an end portion 68 that is configured to fit between selected teeth of an animal patient and to abut various other nontarget teeth in a secure manner, as may be seen upon close examination of FIG. 1.

A connecting member 70 couples support members 64 and 66, and allows distance between the support members to be selectively varied and held fixed. For instance, second support member 66 may be slidably engaged with connecting member 70, such that toggling an angle between support member 66 and connecting member 70 allows the support member to be selectively moved along the length of the connecting member. A spring 72 also may be provided to help conveniently adjust the distance between the support members.

Figure 4:
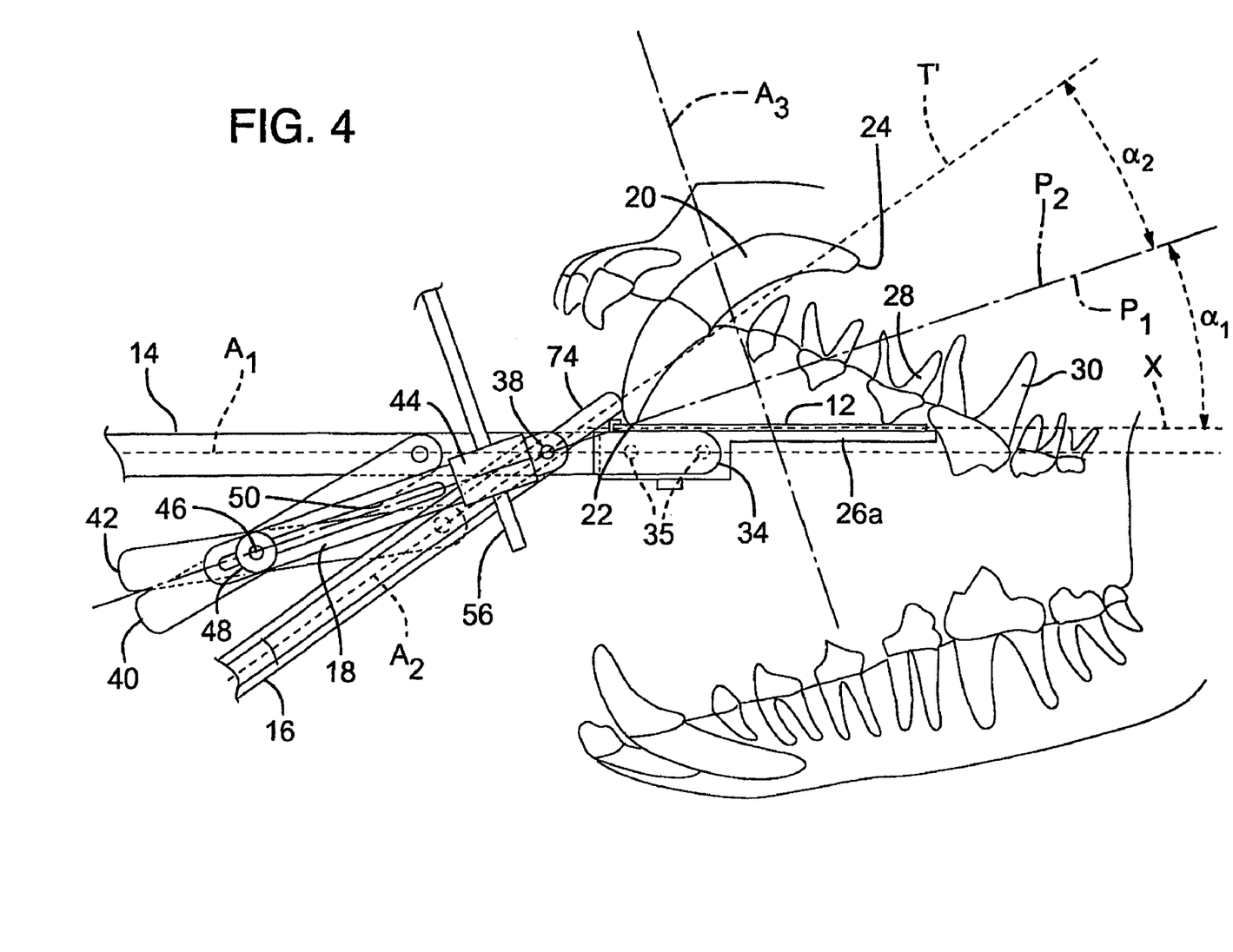
FIG. 4 is another view of the central portion of FIG. 1, showing a guiding member being used to align the instrument with a target plane.

In some embodiments, instrument 10 may include a specialized component for accurately aligning handle 16 with a target plane. For example, FIG. 4 depicts a central portion of instrument 10, including a guiding member 74 built into handle 16 and selectively extendable along axis $A_2$ of the handle. Guiding member 74 may be used to define a target plane, by placing the guiding member against the target tooth and orienting it to point in a desired direction with respect to the tooth. For instance, in FIG. 4, guiding member 74 is shown abutting target tooth 20 and defining a target plane T'. Although plane T' appears substantially parallel to target plane T through tip 22 and apex 24 of the target tooth (compare to FIG. 2), it should be appreciated that guiding member 74 may be used facilitate selection of any desired target plane.

Since in FIG. 4, axis $A_2$ of handle 16 lies in target plane T' (rather than merely parallel to it), the geometry related to the instrument is somewhat simplified. When first handle 14 is engaged with film holder 26a and second handle 16 is placed against the target tooth, axis $A_1$ of handle 14 lies in x-ray film plane X, and axis $A_2$ of handle 16 lies in target plane T'. Bisecting member 18 bisects the angle between the handles, and therefore bisects the angle between the x-ray film plane and the target plane. More specifically, plane $P_2$ bisects the angle between the handles, and therefore coincides with bisecting plane $P_1$. Thus, the bisecting member lies in the bisecting plane, and may be used to facilitate orientation of a collimated x-ray beam in accordance with the bisecting-angle technique, as described previously.

Figure 5:
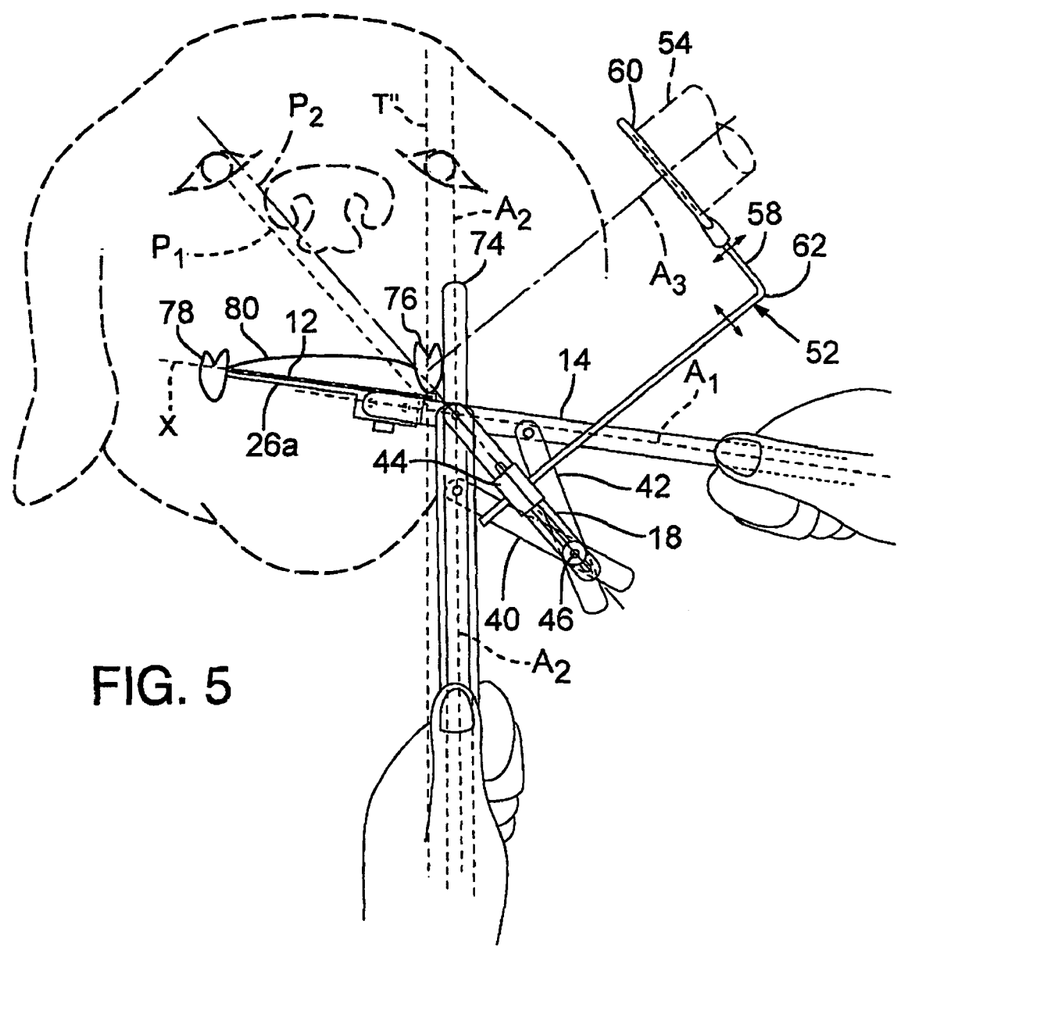
FIG. 5 is another side elevational view of the instrument of FIG. 1, showing the instrument being used to obtain a radiograph of a premolar tooth of an animal patient.

Although FIGS. 1, 2, and 4 depict instrument 10 being used to obtain an x-ray of a canine tooth, in general the instrument may be used to obtain images of various other teeth as well. For example, FIG. 5 shows instrument 10 being used to obtain a maxillary view of a premolar target tooth 76. Premolar target tooth 76 is depicted in FIG. 5 as the patient's fourth maxillary premolar, but instrument 10 and the technique described below may be used to obtain views of any of the molar or premolar teeth. In FIG. 5, only target tooth 76 and a corresponding nontarget premolar tooth 78 are shown for clarity. However, it should be noted that teeth 76 and 78 are in fact disposed behind the canine teeth in the patient's mouth.

As depicted in FIG. 5, instrument 10 is used to obtain a relatively undistorted x-ray image of premolar target tooth 76 in much the same way as it is used when the target tooth is a canine, as previously described and as shown in FIGS. 1–2. In particular, x-ray film 12 is placed in film holder 26a, and the holder is positioned intraorally, adjacent to the target tooth and possibly abutting both nontarget tooth 78 and an upper surface 80 of the patient's palate for stability. Target tooth 76 defines a target plane T", the plane of the film defines an x-ray film plane X, and a film holder support (not shown in FIG. 5) may hold film holder 26a in place during the x-ray procedure.

First handle 14 of instrument 10 engages with film holder 26a, so that longitudinal axis $A_1$ of the first handle is aligned substantially parallel to the x-ray film plane. Second handle 16 is pivoted until longitudinal axis $A_2$ of the second handle is aligned substantially parallel to target plane T". Alignment of the second handle may be facilitated through use of guiding member 74, in this case by positioning guiding member 74 with a lateral edge contacting target tooth 76, as depicted in FIG. 5. This may make it easier for a veterinarian or veterinary technician to accurately orient axis $A_2$ of handle 16 parallel to the target plane.

As previously described, when the instrument has been oriented, axis $A_1$ of handle 14 lies parallel to x-ray film plane X, and axis $A_2$ of handle 16 lies parallel to target plane T". Therefore, plane $P_2$, which bisects the angle between axes $A_1$ and $A_2$, is parallel to bisecting plane $P_1$, which bisects the angle between x-ray film plane X and target plane T". Thus, the bisecting member is oriented parallel to the bisecting plane. X-ray alignment assembly 52, coupled to the bisecting member via mount portion 44, orients longitudinal axis $A_3$ of x-ray collimator 54 such that a collimated x-ray beam will be directed orthogonal to bisecting plane $P_1$, in accordance with the bisecting-angle technique.

While the present description has been provided with reference to the foregoing embodiments, those skilled in the art will understand that many variations may be made therein without departing from the spirit and scope defined in the following claims. The description should be understood to include all novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application. Where the claims recite "a" or "a first" element or the equivalent thereof, such claims should be understood to include incorporation of one or more such elements, neither requiring, nor excluding, two or more such elements.

I claim:

1. An instrument for aligning a collimated x-ray beam relative to an x-ray film and a target tooth of an animal patient to produce dental radiographs in accordance with the bisecting-angle technique, wherein the instrument is configured to align a longitudinal axis of the x-ray beam orthogonal to a bisecting plane lying approximately midway between a target plane defined by the target tooth and an x-ray film plane defined by the x-ray film, comprising:
   a first handle selectively orientable at a first known angle relative to the x-ray film plane;
   a second handle selectively orientable at a second known angle relative to the target plane, wherein orientation of the handles is correlated to alignment of the longitudinal axis of the x-ray beam, wherein the first handle is orientable parallel to the x-ray film plane and the second handle is orientable parallel to the target plane, and wherein the second handle is pivotally attached to the first handle to form a variable angle between the handles to selectively orient the second handle parallel to the target plane; and
   a bisecting member attached to the handles, wherein the bisecting member is oriented substantially parallel to the bisecting plane when the first handle is oriented parallel to the x-ray film plane and the second handle is oriented parallel to the target plane.

2. An instrument as recited in claim 1, wherein the bisecting member is attached to the handles by a pair of rigid coupling members and wherein an equal length of each coupling member separates the bisecting member from the handles.

3. An instrument as recited in claim 2, wherein each coupling member is pivotally attached to one of handles, and wherein the coupling members are pivotally attached to the bisecting member and to each other.

4. An instrument as recited in claim 1, including an x-ray alignment assembly attached to the bisecting member and configured to align an x-ray collimator.

5. An instrument as recited in claim 4, wherein the x-ray alignment assembly includes a first end portion attached to the bisecting member, and a second end portion configured to engage a targeting ring for aligning the x-ray collimator.

6. An instrument as recited in claim 5, wherein the first end portion is attached substantially orthogonally to the bisecting member, and wherein the second end portion is aligned substantially parallel to the bisecting plane when the first handle is oriented parallel to the x-ray film plane and the second handle is oriented parallel to the target plane.

7. An instrument as recited in claim 5, wherein the first end portion is slidably engaged with the bisecting member allowing motion of the x-ray alignment assembly along the longitudinal axis of the x-ray beam.

8. An instrument for aligning a collimated x-ray beam relative to an x-ray film and a target tooth of an animal patient to produce dental radiographs in accordance with the bisecting-angle technigue, wherein the instrument is configured to align a longitudinal axis of the x-ray beam orthogonal to a bisecting plane lying approximately midway between a target plane defined by the target tooth and an x-ray film plane defined by the x-ray film, comprising:
  a first handle selectively orientable at a first known angle relative to the x-ray film plane;
  a second handle selectively orientable at a second known angle relative to the target plane, and wherein orientation of the handles is correlated to alignment of the longitudinal axis of the x-ray beam, wherein the first handle is attachable to a film holder configured to selectively hold the x-ray film against the target tooth; and
  a film holder support including a first support member for selectively engaging and supporting the film holder, a second support member spaced apart from the first support member for engaging one or more non-target teeth, and a connecting member coupling the support members and allowing distance between the support members to be selectively varied and held fixed.

9. A method of aligning an x-ray beam to produce dental radiographs of a target tooth of an animal patient in accordance with the bisecting-angle technigue, wherein an alignment instrument is configured to align a longitudinal axis of the x-ray beam orthogonal to a bisecting plane lying approximately midway between a target plane defined by the target tooth and an x-ray film plane defined by the x-ray film, comprising:
  placing an x-ray film into the patient's mouth;
  attaching the alignment instrument to the x-ray film;
  orienting a first handle of the alignment instrument at a first known angle relative to the x-ray film plane; and
  orienting a second handle of the alignment instrument at a second known angle relative to the target plane
  wherein the steps of orienting the first handle and second handle further orient a reference portion of the alignment instrument at a known reference angle relative to the bisecting plane, and wherein the reference portion is configured to align the longitudinal axis of the x-ray beam at an alignment angle relative to the reference portion and correlated to the reference angle, wherein the first and second angles are both substantially zero, so that the first handle of the instrument is oriented substantially parallel to the x-ray film plane and the second handle of the instrument is oriented substantially parallel to the target plane, and
  wherein the reference portion is a bisecting member attached to the handles, and wherein the bisecting member is oriented substantially parallel to the bisecting plane when the first handle is oriented substantially parallel to the x-ray film plane and the second handle is oriented substantially parallel to the target plane.

10. A method as recited in claim 9, wherein attaching the instrument to the film includes attaching the first handle to a film holder engaged with the film.

11. A method as recited in claim 10, wherein orienting the second handle with the target plane includes pivoting the second handle relative to the first handle.

12. A method as recited in claim 9, wherein orienting the second handle includes placing a guiding member attached to the second handle against the target tooth, and orienting the guiding member to point in a desired direction with respect to the tooth.

13. A method as recited in claim 12, wherein the guiding member is selectively extendable along an axis of the second handle.

14. A method as recited in claim 9, wherein the bisecting member is configured to align an x-ray head targeting ring parallel to the bisecting plane when the bisecting member is oriented substantially parallel to the bisecting plane.

15. A method as recited in claim 9, further comprising holding the x-ray film in place with a compressive force communicated from one or more non-target teeth through a connecting member to the x-ray film.

* * * * *